United States Patent
Garbini et al.

(10) Patent No.: US 9,433,746 B2
(45) Date of Patent: Sep. 6, 2016

(54) MARKERS FOR A MEDICAL ULTRASOUND IMAGING CATHETER

(71) Applicant: Siemens Medical Solutions USA, Inc., Malvern, PA (US)

(72) Inventors: Lex J. Garbini, El Granada, CA (US); Wilko Gerwin Wilkening, Mountain View, CA (US); Ricardo Espinosa, Mountain House, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 14/608,089

(22) Filed: Jan. 28, 2015

(65) Prior Publication Data
US 2015/0143688 A1  May 28, 2015

Related U.S. Application Data

(62) Division of application No. 13/369,236, filed on Feb. 8, 2012, now Pat. No. 8,959,753.

(51) Int. Cl.
*A61M 25/00* (2006.01)
*B29C 65/00* (2006.01)
(Continued)

(52) U.S. Cl.
CPC ............ *A61M 25/0012* (2013.01); *A61B 6/12* (2013.01); *A61B 6/485* (2013.01); *A61B 8/12* (2013.01);
(Continued)

(58) Field of Classification Search
CPC ..... B23B 35/00; B23B 47/28; B23B 47/281; B23B 49/003; B23B 51/0054; B23B 2247/04; B23B 2247/12; B23B 2260/12; B23B 2260/128; B23B 2270/08; B23B 2270/10; B23B 2270/32; B23B 2270/34; B23B 2270/48; B23B 2270/54; B23P 11/00; B23P 11/02; B23Q 17/2291; B29C 66/532; B29L 2031/7542; B29L 2031/7543; A61M 25/0015; A61M 25/0012; A61M 25/0009; A61M 2207/10; A61M 25/0108; G01S 15/04; G01S 15/06; A61B 8/445; A61B 2019/5466; Y10T 29/49005; Y10T 29/49764; Y10T 29/49771; Y10T 29/49774; Y10T 29/49778; Y10T 29/4978; Y10T 29/49888; Y10T 29/49895; Y10T 29/49998

See application file for complete search history.

(56) References Cited

U.S. PATENT DOCUMENTS 2,823,564 A * 2/1958 Lentino .................. B23B 47/281
                                                        408/97
3,605,750 A * 9/1971 Sheridan ............ A61M 25/0108
                                                        138/155
(Continued)

FOREIGN PATENT DOCUMENTS

CN        101670451        3/2010
DE     102006000743 A1 *  7/2007  ............. B23B 41/02

OTHER PUBLICATIONS

Translation of DE 102006000743 A1, generated Oct. 15, 2015.*
(Continued)

*Primary Examiner* — Christopher Besler
*Assistant Examiner* — Matthew P Travers

(57) ABSTRACT

A catheter is provided for medical ultrasound imaging that can be effectively used in combination with other imaging modalities to detect medical structures of interest as well as the catheter. Markers are added to the catheter with precision, which provides a means to merge the images from different modalities. Using a template, apertures for marker placement are formed in the catheter after creating the catheter housing. The ultrasound array may be used for accurate positioning of the template. Alternatively or additionally, a rigid insert with markers connects with the array. The insert holds the markers in place and may reduce artifacts in ultrasound scanning due to flexing of the array.

17 Claims, 3 Drawing Sheets

(51) Int. Cl.
| | |
|---|---|
| *B23B 47/28* | (2006.01) |
| *A61M 25/01* | (2006.01) |
| *A61B 6/00* | (2006.01) |
| *A61B 8/12* | (2006.01) |
| *A61B 6/12* | (2006.01) |
| *A61B 8/00* | (2006.01) |
| *B29L 31/00* | (2006.01) |
| *G01S 15/04* | (2006.01) |
| *G01R 33/48* | (2006.01) |

(52) U.S. Cl.
CPC .......... *A61B 8/445* (2013.01); *A61M 25/0015* (2013.01); *A61M 25/0108* (2013.01); *B23B 47/281* (2013.01); *B29C 66/532* (2013.01); *B23B 2270/48* (2013.01); *B29L 2031/7542* (2013.01); *G01R 33/4814* (2013.01); *G01S 15/04* (2013.01); *Y10T 29/49005* (2015.01); *Y10T 29/49771* (2015.01); *Y10T 29/49778* (2015.01); *Y10T 29/49826* (2015.01); *Y10T 29/49895* (2015.01); *Y10T 29/49945* (2015.01); *Y10T 29/49998* (2015.01); *Y10T 29/5313* (2015.01); *Y10T 29/53087* (2015.01); *Y10T 29/53091* (2015.01); *Y10T 29/53961* (2015.01); *Y10T 408/567* (2015.01)

(56) References Cited

U.S. PATENT DOCUMENTS

| | | | |
|---|---|---|---|
| 3,743,433 A | 7/1973 | Smith | |
| 4,279,252 A | 7/1981 | Martin | |
| 4,554,849 A | 11/1985 | Benham | |
| 5,141,368 A | 8/1992 | Bullard et al. | |
| 5,800,099 A | 9/1998 | Cooper | |
| 5,921,978 A * | 7/1999 | Thompson | A61M 25/0108 604/523 |
| 7,494,467 B2 * | 2/2009 | Makin | A61B 8/12 600/437 |
| 7,783,008 B2 | 8/2010 | Jabri | |
| 2003/0065266 A1 | 4/2003 | Russell | |
| 2006/0173348 A1 * | 8/2006 | Wilser | A61B 8/12 600/466 |
| 2007/0129684 A1 * | 6/2007 | Garbini | A61M 25/00 604/171 |
| 2007/0167825 A1 * | 7/2007 | Lee | A61B 8/12 600/463 |
| 2007/0287957 A1 * | 12/2007 | Magnuson | A61M 25/0012 604/103.1 |
| 2008/0125661 A1 * | 5/2008 | Garbini | A61B 8/483 600/459 |
| 2009/0082665 A1 | 3/2009 | Anderson | |
| 2012/0241076 A1 | 9/2012 | Pingleton et al. | |

OTHER PUBLICATIONS

Machine translation of CN101670451A.

* cited by examiner

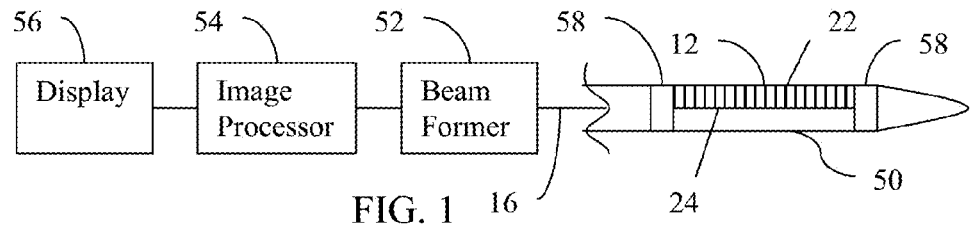
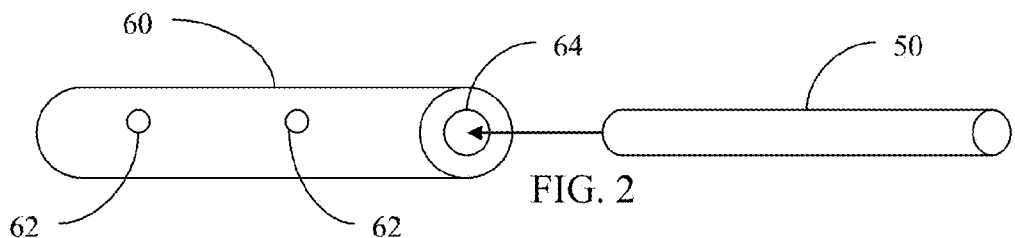
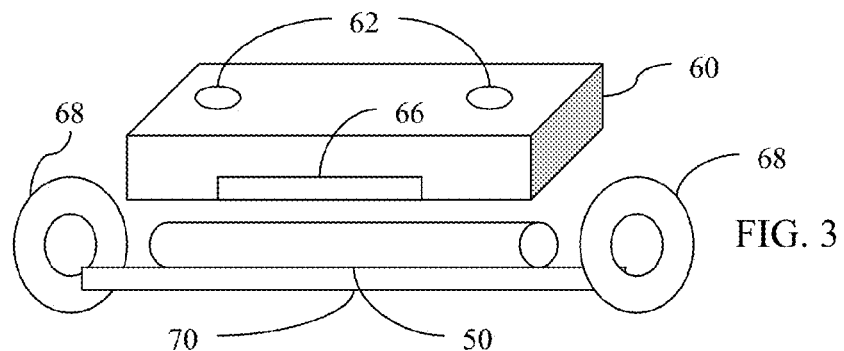
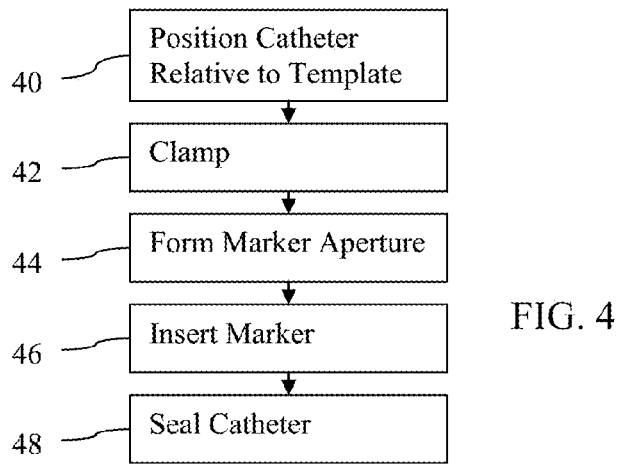
FIG. 4

MARKERS FOR A MEDICAL ULTRASOUND IMAGING CATHETER

CROSS-REFERENCE TO RELATED APPLICATION

This application is a divisional and claims benefit of priority under 35 USC 120 to pending U.S. patent application Ser. No. 13/369,236, filed Feb. 8, 2012.

BACKGROUND

The present embodiments relate to medical ultrasound imaging catheters. An acoustic array is positioned in a catheter. The catheter is positioned in the patient, such as in the heart of the patient. The patient is scanned using the acoustic array, providing real-time images from within the patient. The ultrasound imaging may assist with diagnosis or treatment. However, the flexibility of the acoustic array may result in artifacts in the image. The images may have speckle noise or other artifacts, so it may be difficult for a physician to relate the ultrasound image to the region to diagnose or treat.

Fusing fluoroscopy with the ultrasound imaging provides more information for diagnosis or treatment. The patient and catheter are imaged using x-rays. To register the fluoroscopy imaging with the ultrasound imaging, the catheter is located within a fluoroscopy image. Location of the catheter may be difficult to determine, so radio opaque markers are added to the catheter. The markers allow more precise location identification of the catheter in the fluoroscopy image. Accurate placement of the markers is needed.

The markers are positioned during catheter construction. The catheter housing is formed over the markers and relied on to hold the markers in place. However, the housing is not stable or flows during the construction of the catheter. The markers positioned in the catheter during the construction may change position, leading to inaccuracies in registration of the fluoroscopy and ultrasound images.

For tracking an imaging catheter with magnetic position sensors, a metallic stiffener is provided in the catheter. The stiffener may improve imaging while also improving the orientation of the magnetic position sensors and the acoustic array.

BRIEF SUMMARY

By way of introduction, the preferred embodiments described below include methods, systems, improvements, and catheters for medical ultrasound imaging. Markers are added to the catheter with some precision. Using a template, apertures for marker placement are formed in the catheter after forming of the catheter housing. To position the template before forming the apertures, the ultrasound array may be used. Alternatively or additionally, a rigid insert with markers connects with the array prior to forming the catheter housing. The insert holds the markers in place during flow of the catheter housing and may reduce artifacts in ultrasound scanning due to flexing of the array.

In a first aspect, a method is provided for manufacturing a medical ultrasound imaging catheter. A catheter housing is positioned relative to a template. The catheter housing houses an array of ultrasound elements. The template includes at least one first aperture. The positioning places the first aperture to be near but not on the array. A marker aperture is formed in the catheter housing using the first aperture of the template. A marker is inserted in the marker aperture. The catheter housing is sealed around the marker.

In a second aspect, a system is provided for inserting a marker in a medical ultrasound imaging catheter. A clamp is configured to hold the medical ultrasound imaging catheter in a position relative to a guide. The guide includes a through hole.

In a third aspect, a method is provided for manufacturing a medical ultrasound imaging catheter. An insert is positioned adjacent to a transducer array. The insert has a marker. The transducer array is connected with the insert such that the marker is adjacent to the transducer array in a distal or proximal direction relative to the medical ultrasound imaging catheter. A housing of the medical ultrasound imaging catheter is formed over the transducer array, insert, and marker.

In a fourth aspect, a system is provided for manufacturing a medical ultrasound imaging catheter. An insert has a cavity and at least one marker adjacent to the cavity. A transducer array is sized to fit within the cavity.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for a medical ultrasound imaging catheter;

FIG. 2 is a perspective view of one embodiment of a guide and catheter for manufacturing the catheter with markers;

FIG. 3 is a perspective view of another embodiment of a guide and catheter for manufacturing the catheter with markers;

FIG. 4 is a flow chart diagram of one embodiment of a method for manufacturing a medical ultrasound imaging catheter;

DETAILED DESCRIPTION OF THE DRAWINGS AND PRESENTLY PREFERRED EMBODIMENTS

Figure 5:
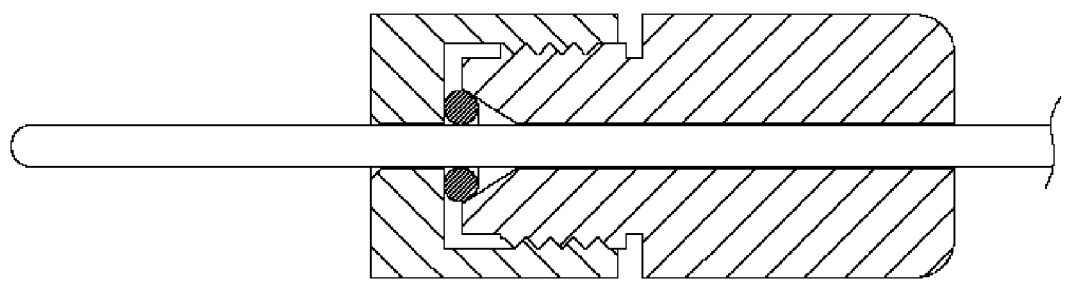
FIG. 5 is a cross-sectional view of a compression fitting for holding the catheter according to one embodiment.

To insert markers within an ultrasound catheter, a cylindrical template fits over the catheter. Holes may be drilled into the plastic catheter body using the cylindrical template as a guide. Markers made from radio opaque material (e.g., tungsten or silver) are inserted into the drilled holes. The markers provide guidance for registration or detection of the catheter in fluoroscopic images.

An additional or alternative approach is to add an insert to the catheter. The insert supports or is connected to the ultrasound transducer array. The insert extends beyond the array distally and/or proximally. One or more markers are in the extension of the insert. The catheter housing is formed over the array, insert, and markers.

While x-ray markers are described herein, other types of markers may be used. For example, the catheter is to be detected in magnetic resonance imaging, optical imaging, or other imaging using non-x-ray radiation. Markers of material with high contrast or opaque to the type of imaging are added to the catheter using the template or added insert.

FIG. 1 shows a system for medical ultrasound imaging with a catheter having markers 58. The ultrasound imaging system is used for diagnosis and/or treatment in combination with another imaging modality, such as an x-ray, fluoroscopy, magnetic resonance, computed tomography, or optical system. Both imaging modalities scan a patient for generating images to assist a physician.

The ultrasound imaging system includes the array 12 of elements 24 for medical ultrasound, a beamformer 52, an image processor 54, and a display 56. Additional, different, or fewer components may be provided. For example, the system includes the array 12 in a catheter 50 without the beamformer 52, image processor 54, and/or display 56. These imaging electronics may be in a separate ultrasound imaging system. The transducer and catheter 50 releasably connect with the imaging system.

The array 12 is used in a transducer probe, such as a medical ultrasound transducer. The transducer is used within a patient, such as a catheter 50, a transesophageal, vaginal, intercavity, intraoperative, or other probe. Alternatively, the transducer probe is used outside of a patient, such as a handheld transducer probe. The array 12 is connected with or positioned in the transducer probe. An acoustic window or lens covers the array 12 to allow acoustic scanning from an emitting face 22 of the array 12 from within the probe. In the catheter embodiments, the window is the housing of the catheter 50.

The array 12 has a plurality of elements 24, backing block, electrodes, and a matching layer. Additional, different, or fewer components may be provided. For example, two or more matching layers are used. The backing block material absorbs acoustic energy to limit or prevent reflections received from the back of the array 12. The matching layers provide a more gradual transition between acoustic impedance, minimizing reflection from the boundary between the transducer and the patient. The electrodes interact with the elements to transduce between acoustic and electrical energy. The variation of potential or distance between electrodes across an element causes electrical signal generation or acoustic energy, respectively.

In one embodiment, flex circuit resides between the backing block and the PZT. The flex circuit bends around the side of the backing block and is folded (in an accordion fashion) behind the backing block. Within the flex connection bundle (accordion), the flex circuit is connected to a bundle of conductors 16 that carry the signals between the beamformer 52 and the array 12. In one variation, the flex connection bundle resides between the backing block and an insert 14 (see FIG. 6).

The elements 24 contain piezoelectric material. Solid or composite piezoelectric materials may be used. Each element is a rectangular solid, cube, or six sided, but other surfaces may be provided. For example, the emitting face 22 of one or more elements 24 is concave or convex for elevation focusing or frequency based directivity. Alternatively, a microelectromechanical device, such as a flexible membrane, is used. Any now known or later developed ultrasound transducer may be used.

Any number of elements 24 may be provided, such as 64 elements. 128 or other number of elements 24 may allow for more or larger apertures. The elements 24 are adjacent to each other, such as having substantially wavelength or less spacing between the centers of adjacent elements 24. For example, the elements 24 have half wavelength spacing with kerfs acoustically separating each element 24. Sparse arrays 12 with greater spacing between elements 24 may be used.

The elements 24 are positioned along an azimuth axis. For a one-dimensional array 12, the elements 24 are in a single row along the azimuth axis. The array 12 may be linear or curved linear. A curved linear array 12 has ends or a middle that extend towards or away from the azimuth axis, but the elements 24 are still positioned along the azimuth dimension. Due to the curve, some elements 24 of the array 12 are at different depths or ranges. For use in a catheter, the azimuth axis is generally along the longitudinal axis of the catheter 50. Generally is used as the array position within the catheter tip is the result of rotation or translation from the axis due to tolerance or manufacturing and/or for purposeful offset along a parallel.

Multi-dimensional arrays 12 may be used. For example, two or more rows of elements 24 are adjacent to each other along the elevation dimension. 1.25, 1.5, 1.75 or 2D arrays may be provided. The spacing between elements 24 along the elevation dimension is the same or different than along the azimuth dimension, such as a 2×64 array with half wavelength spacing between all adjacent elements in azimuth. The elements are long in elevation, such as having a 3-20 wavelength elevation width, but may be half wavelength or have other spacing.

The side of the elements 24 covered by the matching layer, closer to the region to be scanned, and/or opposite the backing block is the emitting face 22. Acoustic energy is transmitted from and received at the emitting face 22 of the array 12. The angle of acoustic energy relative to the emitting face 22 affects the sensitivity of the elements 24 to the energy. The elements 24 are more sensitive to the energy at normal incidence to the elements 24.

Electrical conductors 16 connect the elements 24 of the array 12 to the receive beamformer 52. The conductors 16 are cables, coaxial cables, traces, wires, flex circuits, wire jumpers, combinations thereof, or other now known or later developed conductor. One conductor 16 is provided for each element 24. Alternatively, fewer conductors 16 than elements 24 may be used, such as for switched apertures, partial beamforming, or multiplexing. The conductors 16 are separately addressable. Each element 24 may be selectively used for a given aperture and associated electronic steering. Alternatively, some elements 24 are useable with only a subset of possible apertures.

The array 12 is positioned within the catheter 50. The array 12 may fit within a 10 French, 3.33 mm, or other diameter catheter 50. The conductors 16 are routed through the catheter 50 to the beamformer 52. The catheter transducer is used for imaging. The images assist in diagnosis, catheter or tool guidance, and/or therapy placement.

The markers 58 in the catheter 50 are radio-opaque. Tungsten, silver, gold, stainless steel or other material may be used. The markers 58 are cylinders, but may be other shapes (e.g., spherical, conical, plate, wire, or cube). The markers 58 are any size, such as 0.5 mm diameter cylinder with a 0.5 mm height.

Two markers 58 are shown in FIG. 1. In other embodiments, only one or more than two markers 58 are used. For example, six markers 58 could be used.

The markers 58 are spaced along the catheter 50. As shown, the markers 58 may be positioned adjacent to, but not behind, the array 12. One marker 58 is distal to the array 12, and another marker 58 is proximal to the array 12. Only proximal or only distal markers 58 are provided in other embodiments. Where more than one marker 58 is provided distal or proximal to the array 12, the markers 58 may have an even or variable distribution, such as markers every 2-6 mm. In one embodiment, five markers 58 are placed distal to the array 12 and two markers 58 are placed proximal to the array 12. In alternative embodiments, one or more markers 58 are positioned under or behind the array 12. The markers 58 may be beside or to the sides of the array 12 rather than or in addition to the proximal and/or distal ends.

FIGS. 2 and 3 show a system for inserting a marker 58 in a medical ultrasound imaging catheter 50. The system provides placement of the markers 58 at desired positions during manufacture. The holes for the markers 58 are created in the assembled catheter 50, allowing insertion of the markers 58 into the catheter 50 after formation of the catheter housing about the array 12.

The system includes the catheter 50, a guide 60, a clamp 64, the markers 58, and a measurement device. Additional, different, or fewer components may be used. For example, the measurement device is not provided. As another example, the clamp 64 is not provided.

The guide 60 supports and/or positions the catheter 50 to guide the forming of holes for the markers 58. The guide 60 is a template that fits over or is positionable by the catheter 50. The guide 60 is of any material, such as plastic, metal, wood, or fiberglass.

In the embodiment shown in FIG. 2, the guide 60 is a sleeve. An inner bore is formed for insertion of the catheter 50. The bore is cylindrical, but may have other shapes. The outer portion of the guide 60 is also cylindrical, but may have other shapes. The guide 60 may completely surround the catheter, allowing marker placement at any position. In the embodiment shown in FIG. 3, the guide 60 is a plate.

The guide 60 includes one or more holes 62. The holes 62 are spaced around the guide 60. The holes 62 extend through at least one wall of the guide 60 to allow drilling access to the catheter 50. The guide 60 is a drill guide or template for forming holes in the catheter 50 for the markers 58. The guide 60 has holes 62 that guide a drill or other tool at the correct location and orientation for marker placement.

By inserting the catheter 50 into the bore, the holes 62 are aligned with the desired locations for inserting the markers 58. A stop, such as a closed end of the guide 60, aligns the holes 62 with the catheter 50 as desired. The holes 62 are positioned for forming marker holes in the catheter 50 adjacent to the array 12, such as proximal and distal to the array 12. The holes 62 are positioned to avoid drilling into the array 12.

The array 12 is not always at the same location within the catheter 50. During construction of the catheter 50, various stresses are placed on the array 12 relative to the housing of the catheter 50. As a result of these stresses, the array 12 in the catheter 50 may shift along the longitudinal axis, rotate about the longitudinal axis, and/or rotate away from (no longer parallel with) the longitudinal axis. As a result, the holes 62 of the guide 60 may not be positioned at consistent locations relative to the array 12. This may be acceptable in many embodiments.

For embodiments where a greater accuracy of position of the markers 58 relative to the array 12 is desired, the guide 60 may be oversized. For example, the bore allows rotation about, rotation away, and/or translation along the longitudinal axis of the catheter 50 relative to the guide 60. The bore is large enough to allow shifting of the catheter 50 relative to the guide 60 and corresponding holes 62.

To place the array 12 at the correct position relative to the holes 62 even while the array 12 is covered by the housing of the catheter 50 and/or the guide 60, an acoustic target 66 is provided in the guide 60. The acoustic target 66 is a metal or other acoustically reflective piece. For example, the acoustic target 66 is stainless steel. Alternatively, the guide 60 is reflective and the target is more acoustically transparent.

The acoustic target 66 is a plate or sheet of material. Other shapes may be used, such as a wire or one or more spheres. While shown as just one piece, multiple acoustic targets 66 may be provided. Combinations of shapes may be used. The target 66 has any size, such as having a similar area as the array 12.

The acoustic target 66 is on a surface of the guide 60 closest to the bore or location where the catheter 50 is to be placed. Alternatively, the acoustic target 66 is embedded within the guide 60 or is on a surface spaced from the catheter 50.

The acoustic target 66 is positioned within or on the guide 60 at a location detectable with the array 12. By acoustically measuring with the array 12, the position of the array 12 relative to the acoustic target 66 is determined. The array 12 may be aligned with the acoustic target 66, aligning the array 12 relative to the holes 62.

The clamp 64 is sized and shaped to hold the catheter 50 in a position relative to the guide 60. The clamp 64 holds the catheter 50 with the holes 62 aligned relative to the array 12 or the catheter 50.

The clamp 64 of FIG. 2 is the bore. The bore is sized to hold the catheter 50 in position. For example, the bore is sized to allow insertion of the catheter 50 but establishing friction when inserting.

Other clamps 64 may be used. FIG. 3 shows another clamp 68. Two clamps 68 connect with a plate 70 or other structure for supporting the catheter 50 during forming of the marker holes. The clamps 68 hold the catheter 50 by compression, such as using spring force, compression fitting, being sized about a same size as the catheter 50, one or more screws, or other clamping structure.

The clamp 68 may hold the catheter 50 relative to the guide 60. Both the guide 60 and the clamps 68 are connected with a table, ground, or other relatively immobile base. The same or different bases may be used. The clamps 68 may connect through support structure with the guide 60 or may be separately connected to the ground. The clamps 68 and/or the guide 60 are moveable relative to their supporting bases.

The clamp 68 may hold the catheter 50 relative to the guide 60 in various positions. The positions include different lateral locations along the longitudinal axis. A guide (e.g., tongue and groove) may be used for this translational motion. The positions include different rotation about the longitudinal axis. The clamps 68 may be released or have a soft enough hold that the catheter 50 may be rotated about the longitudinal axis. The positions include different rotation from the longitudinal axis. The clamps 68 or guide 60 may be supported by a rotatable base to allow changing of the angle of the catheter 50 relative to the guide 60.

The various degrees of freedom of the clamps 68 relative to the guide 60 allow adjustment of the catheter 50 relative to the guide 60. The adjustment may account for the variation in the position of the array 12 within different catheters 50. Once positioned, the various moveable components may be locked, such as using a brake or screw, for forming the marker holes.

FIG. 5 shows another clamp. The clamp is a compression fitting. For example, the guide 60 of FIG. 2 includes threading. The threading is on an outer circumference or in the bore. A fitting with an o-ring slides over the catheter 50 and mates with the threading. The force from screwing the pieces together places holding pressure on the o-ring and catheter 50. For example, once the catheter 50 is in the desired position within the bore, the catheter 50 is locked into place by tightening the compression fitting. Shims, injectable foam, or other devices may be used to hold the catheter 50 in place during tightening of the clamp or forming the marker apertures.

Referring again to the embodiment of FIG. 3, the catheter 50 is positioned relative to the guide 60 and holes 62 by moving the clamp 68 or clamps 68, moving the guide 60, and/or rotating the catheter 50 within the clamps 68. The change in position may be determined by a measurement device. The measurement device is configured to indicate the position of the array 12 relative to the acoustic target 66.

In one embodiment, the measurement device is an infrared or optical scanner. The catheter 50 is semi-transparent. Shining light through the catheter 50 may allow a user or a system to orient the array 12. For example, an optical image showing the array 12 within the catheter 50 is used by a processor to identify the array 12 and control motors for positioning the array 12 relative to the guide 60. This operation may work without the acoustic target 66. X-rays may be used. Fluoroscopy in patients is limited to low radiation level or short exposure times. However, more accurate X-ray imaging devices may be used in production, and such systems image the array with sufficient resolution to exactly determine location and orientation. While positioning the markers correctly is very desirable, such an imaging system may alternatively be used to determine the exact marker position relative to the array in order to determine a correction term (e.g., deviation from desired location). This information may be stored in the ultrasound system or navigation system.

In an embodiment using the acoustic target 66, the ultrasound system is used as the measurement device. The array 12 is a sensor. The beamformer 52 and image processor 54 measure the location of the acoustic target 66 relative to the array 12. A coupling gel or water is placed between the outside of the catheter 50 and the acoustic target 66. Acoustic energy is used to measure the distance and rotation of the array 12 relative to the acoustic target 66. The rotation of the catheter 50 may be adjusted to achieve a peak or maximum signal. When the array 12 is more directly facing the target 66, the return signal may be greater due to the elevation focus. By alternating transmissions and reception between distal and proximal elements 24, the distance from the elements 24 to the target 66 may be determined. The catheter 50 or guide 60 is rotated to even the distances. Similarly, the end elements 24 may be used to adjust the catheter 50 by translation along the longitudinal axis. The peak or maximum signal indicates proper alignment.

The adjustments may be performed iteratively. A processor may control the adjustments or the adjustments are handled manually. The ultrasound generated by the catheter 50 is used to position the acoustic array 12 parallel to a planar target 66.

Once the array 12 is parallel to the target 66, the clamps 68 are locked in position. Alternatively, a sleeve is positioned over the catheter 50 and temporarily fixed into position.

With the clamps 64, 68 locked, the marker holes are formed. The guide 60 guides the drill, laser, heated rod, or other device for forming the marker holes. The marker holes are formed in the housing of the catheter 50 at the desired locations.

With the catheter 50 still in the guide 60 or after removing the catheter 50 from the clamps 64, 68 and/or guide 60, the radio-opaque markers 58 are placed into the marker holes. The markers 58 are inserted into the catheter 50. The marker apertures may be large enough that the markers 58 loosely fit. Alternatively, pressure is used to insert the markers 58 into tightly fitting marker apertures. In yet another embodiment, the markers 58 are heated and used to both form the marker aperture and be inserted. The markers 58 are cut from a wire or detached.

At least some of the markers 58 are adjacent to the array 12. The markers 58 may contact the array, be spaced within 3 mm, or be at another distance from the array 12.

The catheter housing is sealed over the markers 58. After sealing, the catheter 50 may be used for imaging. Referring again to FIG. 1, the array 12 connects to the beamformer 52 for imaging. The beamformer 52 includes a plurality of channels for generating transmit waveforms and/or receiving signals. Relative delays and/or apodization focus the transmit waveforms or received signals for forming beams. The beamformer 52 connects with the conductors 16. The beamformer 52 selects an aperture including one, some, or all of the elements 24 of the array 12. Different apertures may be used at different times. The aperture is formed by using the elements 24 for transmit and/or receive operations while not using other elements. The beamformer 52 is operable to scan from a plurality of apertures formed by adjacent groups of the elements 24. The apertures may walk through regular increments or skip to different portions of the array 12.

For scanning, the beamformer 52 electronically focuses along the azimuth direction. A plurality of scan lines using an aperture is scanned. During receive operations, the focus may vary as a function of depth (i.e., dynamic focusing). An elevation focus is provided by a lens and/or element sensitivity, or the array 12 is not focused in elevation. In alternative embodiments, the beamformer 52 connects with elevation spaced elements for at least partial electric focusing and/or steering in the elevation dimension.

The image processor 54 is a detector, filter, processor, application specific integrated circuit, field programmable gate array, digital signal processor, control processor, scan converter, three-dimensional image processor, graphics processing unit, analog circuit, digital circuit, or combinations thereof. The image processor 54 receives beamformed data and generates images on the display 56. The images are associated with a two-dimensional scan. Alternatively or additionally, the images are three-dimensional representations. Data representing a volume is acquired by scanning.

Using the markers 58, the array 12 may be located in other imaging. For example, x-rays for fluoroscopy are transmitted through the patient with the catheter 50 in the patient. The markers 58 are radio-opaque, so appear as bright or contrast objects in the fluoroscopic image or detected data. Since the position of the array 12 relative to the markers 58 is known, such as based on the positioning provided by the guide 60, the location and/or orientation of the array 12 is determined from the markers 58.

FIG. 4 shows a method for manufacturing a medical ultrasound imaging catheter. The method uses the system of FIGS. 1, 2, 3, and/or 5. Additional, different, or fewer acts may be provided. For example, the clamping of act 42 is not done, but instead the catheter is held by the user. As another example, the marker apertures are formed in act 44, but the markers are not yet inserted in act 46 and/or the catheter sealed in act 48.

In act 40, the catheter housing is positioned relative to a template. The catheter housing covers or houses an array of ultrasound transducer elements, the associated cables, and any steering wires. Around the array and at the tip, the catheter housing may be more rigid or thicker.

The positioning is manual or automatic. Using motors or a user, the catheter housing is adjusted laterally and/or rotated about any number of axes. For example, rotation about at least two axes, the longitudinal axis and a perpendicular axis, is provided.

The positioning places apertures of the template at desired locations relative to the array and/or catheter housing. For example, the apertures in the template are positioned for forming holes in the housing near to but not in the acoustic path of the array. Near may be within 2 mm. Other locations may be used, such as under the array or spaced from the array. Any number of apertures may be used.

In one embodiment, the catheter housing is positioned relative to the template by placement in a guide. For example, a cylindrical sleeve guides the catheter housing. Stops are used to position the catheter housing in the cylindrical housing. The catheter housing slides into the guide, such as a sleeve, until a stop prevents further sliding. As another example, stops are not used. Instead, the catheter housing is positioned in one or more clamps. The clamps guide the catheter housing.

With the guide or without a guide, the array within the catheter housing is aligned relative to the template. The alignment occurs based on the guide and stops. Alternatively, the alignment is more exact, relying on the identification of the location of the array. Using optical imaging, a sensor, or the array itself, the array is aligned with the template. For example, the signal strength, distance from a reflector, or other signal characteristic indicates the position of the array to the template or a target on the template. The information is used to align the array with the template.

The catheter housing, the guide, the clamps, a support base, the template, and/or the holes in the template are moved for relative positioning. The movement may be manual or by a motor or pressure (e.g., pneumatics).

Once positioned as desired, the clamps prevent further movement. The moveable component or components (e.g., the catheter, guide, or clamps) are locked or braked in act 42. A thumb screw may be tightened. Spring activation, bolt closing, application of pressure, or other clamping may be used.

In one embodiment, the catheter housing is clamped. This clamping may prevent further translation and/or rotation. A guide, the template, the clamps themselves or other component may also be locked or clamped to prevent further movement. The catheter housing is clamped in position relative to the template.

In another embodiment, the clamping is performed with a compression fitting. By turning a threaded guide, closure, or other device, an o-ring may press against the catheter housing.

Once clamped, one or more marker apertures are formed in act 44. The marker apertures are formed in the catheter housing. The apertures in the template indicate the location and orientation of the marker apertures. Alternatively, the orientation is assumed or treated as normal to the axis of the catheter 50. The apertures of the template guide the formation of the marker apertures.

The marker apertures are formed by drilling, cutting, etching, melting, or other process. For example, the apertures of the template guide a drill to the catheter housing. The drill may be zeroed at any location. The position of the drill relative to the catheter housing is calibrated. For example, the drill bit is placed in contact with the catheter housing. Based on this location of the drill, a marker aperture may be formed in the catheter housing or catheter to a desired depth. A dial indicator or other measurement determines the depth from the zeroed location. The depth may be sufficient to allow sealing of the marker within the catheter housing. The drill is activated to drill through the catheter housing and into the catheter. The catheter housing may be solid other than internal components of the catheter, such as where the catheter housing is melted or flows to fill any gaps.

In act 46, a marker is inserted within each marker aperture. The marker is inserted using a pick and place process, such as by a robot or gravity feed device. Alternatively, the markers are manually inserted into the marker apertures.

The markers are inserted with the template in place. The markers pass through the apertures of the template and into the marker apertures of the catheter housing. Alternatively, the template or guide is removed. The catheter may be unclamped and removed or may remain clamped. The markers are inserted into the catheter housing directly or without passing through the apertures of the template.

In act 48, the catheter housing is sealed around the marker. Additional housing material, such as plastic (e.g., Pebax®), is added to cover the marker and hole. The material is the same or different than the material used to form the catheter housing. Alternatively, no additional material is added.

To seal, heat is applied. The housing material or additional material is heated to or near a melting point. The heated material flows to fill gaps and seal the hole. In alternative embodiments, a viscous material, such as ultra-violet curable silicone, is added and cured to seal. Epoxy or other sealing adhesives may be used without heating to avoid further change in the array position within the catheter or further melting of the catheter housing.

Figure 6:
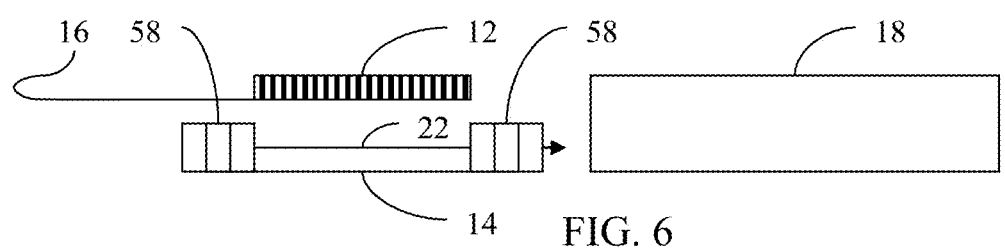
FIG. 6 is a side view of one embodiment of a system for manufacturing a medical ultrasound imaging catheter.

FIG. 6 shows another embodiment of a system for manufacturing a medical ultrasound imaging catheter. The system uses an insert 14 added to the transducer stack prior to encasing in the catheter housing 18 rather than markers added after encasing.

The system includes the insert 14, the array 12, cables 16, markers 58, and the catheter housing 18. Additional, different, or fewer components may be provided. For example, additional markers 58 are provided.

The insert 14 is a material in addition to the transducer stack. The transducer stack of the array 12 includes the matching layer, electrodes, flexible circuits, and backing block. The insert 14 may incorporate the backing block and/or signal traces for connecting the electrodes to the cables 16 or may not. The insert extends beyond the array, such as distally and/or proximally along the axis of the catheter 50 being assembled. The insert 14 is a separate component from the array 12.

The insert 14 is plastic, but other materials may be used. In one embodiment, the insert 14 is formed from high Tg (glass transition temperature) plastic (e.g., PSU Tg=190 C). The melt temperature is 10 degrees or more above the melt temperature of the catheter housing 18, such as being substantially higher than the melt temperature of Pebax®. The greater melt temperature may avoid compromising the marker placement during subsequent tipping of the catheter. By having a greater melt temperature, the insert 14 does not flow or reach a melting point even when the catheter 50 is heated to form the catheter housing 18. The insert 14 may not change shape during the plastic welding or casting used to fabricate the catheter 50.

The insert 14 includes a cavity 22. The cavity 22 is sized to form or press fit around the array 12. Beams, walls, or other structure on at least two sides hold the array 12 by friction, snap fit, or other connector. In one embodiment, the cavity 22 press fits with the array 12 on four sides. The cavity 22 may instead be oversized relative to the array 12. A connector or adhesive holds the array 12 to the insert 14, such as on a side wall or bottom surface of the cavity 22. In yet other embodiments, the insert 14 is free of a cavity for the array 12, and the array 12 connects to a top surface of the insert 14. The cavity 22 may be a hole in the insert, surrounding the array 12 on only 2-4 sides.

The insert 14 is more rigid than the array 12. For example, the plastic or other material bends less in response to the same stress as the array 12 along the longitudinal axis. Beams, ridges or other structure in addition to or as an alternative to more rigid material may be used to make the insert 14 more rigid than the array 12. By connecting the insert 14 to the array 12, the geometry established by the insert 14 may assist in imaging. Maintenance of the array 12 as flat, curved or some other shape within the catheter 50 may reduce imaging artifacts and/or allow sector scanning. The bow or curvature of the array 12 may be minimized by introducing the insert 14 as a reinforcing member. The insert 14 may reduce any curvature along the longitudinal axis of the array or may enforce a desired curvature.

The insert 14 includes at least one, some of, or all of the markers 58 for the catheter 50. The markers 58 are placed in apertures cast, drilled, or formed in the insert 14. The portion of the insert 14 extending beyond the array 12 is used to support the markers. The bottom or portion under the array 12 may alternatively or additionally support one or more markers 58. Alternatively, the markers 58 are formed in the insert 14, such as being cast in the insert 14. In yet other embodiments, the markers 58 are bonded to the insert 14 without placement in an aperture.

None of the guides of FIG. 2, 3, or 5 would be needed where the insert includes all of the markers. The template would not be required to place the markers 58 already positioned within the insert 14. Additional markers may be added using the template.

Since the insert is positioned and connected with the array 12, the position of the markers 58 relative to the array is established with precision. The insert 14 captures the array 12 during assembly of the catheter 50, as well as to create an extended rigid body that contains the markers 58. The markers 58 are precisely positioned prior to plastic welding the acoustic array 12 to the catheter housing 18. The radio-opaque markers 58 may be accurately attached to the insert 14.

The catheter housing 18 is a sleeve of plastic or other material for insertion into a patient. For example, the catheter housing 18 is formed from Pebax®. Other materials may be used.

The catheter housing 18 is placed over the array 12 and insert 14, after the array 12 and insert 14 are connected together. The catheter housing 18 slides over the array 12, insert 14, markers 58, and some of the extent of the cables 16. In one embodiment, the catheter housing 18 is plastic welded as a thermoplastic around the array 12 and insert 14. Epoxy or other bonding agent may be provided between the catheter housing 18 and the array 12. Multiple layers of housing material may be used, such as one layer for electrical insulation and another for the outer surface of the catheter 50.

Figure 7:
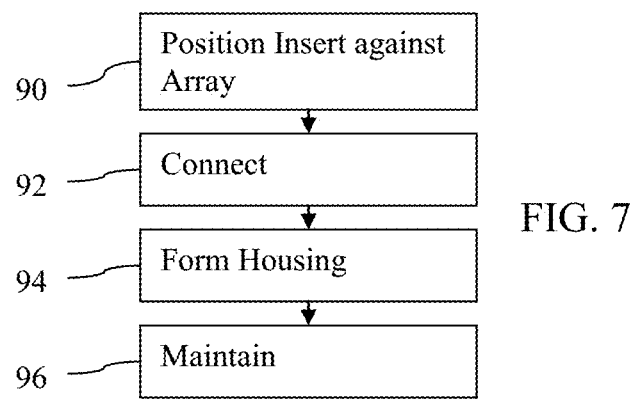
FIG. 7 is a flow chart diagram of one embodiment of a method for manufacturing a medical ultrasound imaging catheter.

FIG. 7 is a flow chart diagram of one embodiment of a method for manufacturing a medical ultrasound imaging catheter. The method uses the system of FIG. 6 or other system for assembling the catheter. Additional, different, or fewer acts may be provided. For example, the acts of the method of FIG. 4 are also provided so that markers are placed using the insert prior to forming the catheter housing and placed using a guide after the catheter housing has been formed. As another example, act 96 is not performed. Instead, the insert has more or a similar flexibility as the array. The acts are performed in the order shown or a different order.

In act 90, the insert is positioned adjacent to a transducer array. For example, the transducer array is placed or pressed into a cavity of the insert. Fiducials, guides, rails, posts, holes, or other structures may be provided for positioning the insert relative to the array. The insert and the array mate or slide together in one relative position.

The placement of the insert against the array positions one or more markers relative to the array. For example, one or more markers are in the insert against or adjacent to the cavity. By placing the array in the cavity, the marker is positioned adjacent to the array. The marker is adjacent to the transducer array in a distal or proximal direction relative to the medical ultrasound imaging catheter. The marker may instead be beside or under the array.

In act 92, the transducer array is connected with the insert. The connection may be by friction, such as a press fit of the array to the insert (e.g., cavity). Latches, snap fit, or other connectors (e.g., screw) may be used. Alternatively or additionally, the array is bonded to the insert with adhesive. For example, the array connects to the insert by bonding, such as with epoxy cured at room temperature or higher temperatures (e.g., 50 degrees Celsius). After stacking the insert with the array, the stack is pressed and cured to fix the array to the insert. The adhesive is applied before positioning the array against the insert. Alternatively, the adhesive is applied after positioning, such as for formation of the catheter housing.

The connecting fixes the transducer array to the insert. The array does not move relative to the insert after the fixing. The fixing occurs before or after addition of the catheter housing. The insert connects with the array directly or through one or more other components. For example, the insert is stacked with an array of matching layer, transducer material, and backing block. Conductors, such as a flexible circuit extend from between the transducer material and the backing block. The bundle or accordion bundle of flexible circuit material is positioned behind the backing block. The insert is stacked directly against the backing block or the bundle or accordion of flexible circuit material is between the insert and the array.

In act 94, the catheter housing is formed. The housing is formed over the transducer array, insert, and any markers in the insert. The transducer array and insert are placed into the housing, such as sliding a sleeve of housing material over the array. By heating the housing substantially to a melting point of the housing, the catheter housing flows into gaps and over the components of the catheter. Since the insert has a higher melting point than the Tg of the housing, the insert maintains position relative to the array. The insert and array remain flat despite the heating of the catheter housing.

Some portions of the catheter housing 18 before assembly and/or after assembly may be thicker. Thicker material may be used to provide more rigidity. In extruding the catheter housing, forming thicker regions may be difficult. Thin wall sections are desired around the sides of the array. It is difficult to move plastic via injection molding to form thick wall sections beyond the thin wall sections. The insert does not require thick wall sections, so the tip or housing may be easier to manufacture. Using the insert for rigidity may avoid providing a thicker housing for a large region that may otherwise use a thicker housing. Alternatively, thicker housing material is provided for around the insert.

In act 96, the transducer array is maintained substantially flat. While the insert and connected array may bow or bend under some stresses during use, the array bends less or requires greater force to bend due to the connected insert. Since the insert is more rigid than the transducer array, the array may be held in a more consistent configuration (e.g., flat) during use to scan from within the patient. This added rigidity may also apply during the tipping process where high hydrostatic pressures and sometime off-axis compressive forces bend, bow, or otherwise distort the array. Fewer image artifacts may result.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for manufacturing a medical ultrasound imaging catheter, the method comprising:
positioning a formed catheter housing relative to a template, the catheter housing housing an array of ultrasound elements, and the template including at least one first aperture, the positioning being of the first aperture to be near but not on the array;
forming a marker aperture in the catheter housing using the first aperture of the template;
inserting a marker in the marker aperture of the formed catheter housing; and
sealing the marker aperture of the catheter housing around the marker with additional material or material from the formed catheter housing existing prior to the inserting, wherein the sealing is performed after the inserting into the formed catheter housing;
wherein positioning comprises aligning the array relative to the template, and wherein aligning comprises sensing with the array a position of the array relative to the template.

2. The method of claim 1 wherein the template comprises a cylindrical sleeve, and wherein positioning comprises placing the catheter housing in the cylindrical sleeve.

3. The method of claim 2 wherein placing comprises sliding the catheter housing into the cylindrical housing until a stop in the cylindrical sleeve prevents further sliding.

4. The method of claim 1 wherein forming comprises guiding a drill with the first aperture and drilling through the catheter housing.

5. The method of claim 4 wherein forming comprises zeroing the drill relative to the catheter housing, and wherein drilling comprises drilling to a predetermined depth.

6. The method of claim 1 wherein inserting comprises removing the template and placing the marker into the marker aperture.

7. The method of claim 1 wherein sealing comprises heating the catheter housing.

8. The method of claim 1 wherein the marker comprises a material opaque to x-rays and wherein inserting comprises inserting the material.

9. The method of claim 1 further comprising:
clamping the catheter housing relative to the template with a compression fitting.

10. A method for manufacturing a medical ultrasound imaging catheter, the method comprising:
positioning a catheter housing relative to a template, the catheter housing housing an array of ultrasound elements, and the template including at least one first aperture, the positioning being of the first aperture to be near but not on the array;
forming a marker aperture in the catheter housing using the first aperture of the template;
inserting a marker in the marker aperture; and
sealing the catheter housing around the marker;
wherein positioning comprises:
sensing, by a beamformer and image processor connected with the array, an acoustic target having a different acoustic reflectivity than material of the template supporting the acoustic target, the sensing being of a position of the array relative to the template, the position indicating a first alignment of the array based on a peak in acoustic response received by the beamformer from the array; and
aligning the array relative to the template based on the sensing.

11. The method of claim 10 wherein the template comprises a cylindrical sleeve, and wherein positioning comprises placing the catheter housing in the cylindrical sleeve.

12. The method of claim 10 wherein forming comprises guiding a drill with the first aperture, zeroing the drill relative to the catheter housing, and drilling through the catheter housing to a predetermined depth.

13. The method of claim 10 wherein the marker comprises a material opaque to x-rays, and wherein inserting comprises removing the template and placing the marker into the marker aperture.

14. The method of claim 10 wherein sealing comprises heating the catheter housing.

15. The method of claim 10 further comprising:
clamping the catheter housing relative to the template with a compression fitting.

16. A method for manufacturing a medical ultrasound imaging catheter, the method comprising:
positioning a catheter housing relative to a template, the catheter housing housing an array of ultrasound elements, and the template including a plurality of guide apertures, the positioning being of the guide apertures to be near but not on the array;
forming marker apertures in the catheter housing using the plurality of guide apertures of the template;
inserting markers in the marker apertures; and
sealing the catheter housing around the markers;
wherein positioning comprises positioning based on measurement by the array of an acoustic response of an acoustic target of the template.

17. The method of claim 16 wherein forming comprises guiding a drill with one of the plurality of guide apertures, zeroing the drill relative to the catheter housing, and drilling through the catheter housing to a predetermined depth.

* * * * *